US009743855B2

(12) United States Patent
Freeman et al.

(10) Patent No.: US 9,743,855 B2
(45) Date of Patent: Aug. 29, 2017

(54) RESUSCITATION ENHANCEMENTS

(71) Applicant: ZOLL MEDICAL CORPORATION, Chelmsford, MA (US)

(72) Inventors: Gary A. Freeman, Waltham, MA (US); Ulrich Herken, Medford, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

(21) Appl. No.: 14/594,529

(22) Filed: Jan. 12, 2015

(65) Prior Publication Data

US 2015/0126885 A1 May 7, 2015

Related U.S. Application Data

(63) Continuation of application No. 13/493,276, filed on Jun. 11, 2012, now Pat. No. 8,948,859.

(51) Int. Cl.
*A61B 5/04* (2006.01)
*A61B 5/046* (2006.01)
(Continued)

(52) U.S. Cl.
CPC ............ *A61B 5/046* (2013.01); *A61B 5/0245* (2013.01); *A61B 5/4836* (2013.01);
(Continued)

(58) Field of Classification Search
CPC ..... A61B 5/0205; A61B 5/0245; A61B 5/046; A61B 5/4836; A61B 5/4839;
(Continued)

(56) References Cited

U.S. PATENT DOCUMENTS 5,077,667 A 12/1991 Brown et al.
5,741,304 A 4/1998 Patwardhan et al.
(Continued)

FOREIGN PATENT DOCUMENTS

WO 2011/100534 8/2011

OTHER PUBLICATIONS

International Search Report and Written Opinion from corresponding PCT/US2013/44750 mailed Sep. 20, 2013.
Extended European Search Report, European Patent Application No. 13804051.4, dated Feb. 4, 2016, 9 pages.
(Continued)

*Primary Examiner* — Lindsey G Wehrheim
(74) *Attorney, Agent, or Firm* — Fish & Richardson P.C.

(57) ABSTRACT

A system including a sensor interface coupled to a processor. The sensor interface is configured to receive and process an analog electrocardiogram signal of a subject and provide a digitized electrocardiogram signal sampled over a first time period and a second time period that is subsequent to the first time period. The processor is configured to receive the digitized electrocardiogram signal, to analyze a frequency domain transform of the digitized electrocardiogram signal sampled over the first and second time periods and determine first and second metrics indicative of metabolic state of a myocardium of the subject during the first and second time periods, respectively, to compare the first and second metrics to determine whether the metabolic state of the myocardium of the subject is improving, and to indicate administration of an intervention to the subject in response to a determination that the metabolic state is not improving.

17 Claims, 3 Drawing Sheets

(51) Int. Cl.
  *A61N 1/39* (2006.01)
  *A61B 5/0245* (2006.01)
  *A61B 5/00* (2006.01)
  *A61B 5/0205* (2006.01)
  *A61H 31/00* (2006.01)

(52) U.S. Cl.
  CPC .......... *A61B 5/7275* (2013.01); *A61N 1/3925* (2013.01); *A61B 5/0205* (2013.01); *A61B 5/4839* (2013.01); *A61B 5/4848* (2013.01); *A61B 5/7257* (2013.01); *A61H 31/005* (2013.01); *A61H 2230/045* (2013.01)

(58) Field of Classification Search
  CPC ... A61B 5/4848; A61B 5/7257; A61B 5/7275; A61H 2230/045; A61H 31/005; A61N 1/3925
  See application file for complete search history.

(56) References Cited

U.S. PATENT DOCUMENTS

| | | | |
|---|---|---|---|
| 5,957,856 A * | 9/1999 | Weil | A61N 1/39 600/518 |
| 7,269,454 B2 | 9/2007 | Sherman | |
| 7,831,299 B2 | 11/2010 | Tan et al. | |
| 8,165,671 B2 | 4/2012 | Freeman et al. | |
| 2005/0245974 A1 | 11/2005 | Sherman | |
| 2007/0060785 A1 | 3/2007 | Freeman et al. | |
| 2009/0281413 A1* | 11/2009 | Boyden | A61B 5/0059 600/407 |
| 2010/0268059 A1 | 10/2010 | Ryu et al. | |

OTHER PUBLICATIONS

Supplementary European Search Report, European Patent Application No. 13804051.4, dated Feb. 23, 2016, 10 pages.

\* cited by examiner

RESUSCITATION ENHANCEMENTS

RELATED APPLICATIONS

This application claims the benefit under 35 U.S.C. §120 as a continuation of U.S. application Ser. No. 13/493,276, titled "RESUSCITATION ENHANCEMENTS," filed on Jun. 11, 2012, which is herein incorporated by reference in its entirety.

BACKGROUND OF INVENTION

1. Field of Invention

Aspects and embodiments of the present invention are directed to the use of spectral analysis of Ventricular Fibrillation (VF) waveforms to aid in the resuscitation of a subject experiencing cardiac arrest.

2. Background

Cardiac arrest is a major cause of death worldwide. Various resuscitation efforts aim to maintain the body's circulatory and respiratory systems during cardiac arrest in an attempt to save the life of the subject. Such resuscitation efforts may include CPR (i.e., chest compressions with or without artificial respiration), defibrillation, drug therapy, open heart massage, or various combinations thereof. For many forms of cardiac arrest, such as where the subject is suffering from Ventricular Fibrillation (VF) or Ventricular Tachycardia (VT), defibrillation may be appropriate, especially if applied soon after the onset of VF or VT. However, because defibrillation can itself cause myocardial injury, it should generally be applied only when there is a sufficient probability of success that it will be successful in restoring a perfusing cardiac rhythm.

U.S. Pat. No. 5,957,856 (hereinafter the '856 patent), which is incorporated by reference in its entirety herein, discloses a system and method for predicting the success of a defibrillating shock based upon a spectral analysis of VF waveforms obtained from an electrocardiogram (ECG) of the subject. As described therein, various metrics, such as the average peak-to-trough amplitude (AM) of the VF waveform, the area of the amplitude spectrum (ASA or AMSA) of the VF waveform, the median frequency of the power spectrum of the VF waveform, or the area of the power spectrum (PSA) of the VF waveform may be used to predict when defibrillation is likely to be successful in restoring a perfusing cardiac rhythm, as well as when defibrillation is likely to not be successful.

SUMMARY

In accordance with one aspect of the present invention, a system is provided that includes a sensor interface and a processor. The sensor interface is configured to receive and process an analog electrocardiogram signal of the subject and provide a digitized electrocardiogram signal sampled over a first time period and a second time period that is subsequent to the first time period. The processor is coupled to the sensor interface and is configured to receive the digitized electrocardiogram signal, to analyze a frequency domain transform of the digitized electrocardiogram signal sampled over the first time period and the second time period and determine first and second metrics indicative of metabolic state of a myocardium of the subject during the first and second time periods, respectively, to compare the first and second metrics to determine whether the metabolic state of the myocardium of the subject is improving, and to indicate administration of a thrombolytic agent to the subject in response to a determination that the metabolic state of the myocardium of the subject is not improving.

In accordance with another aspect of the present invention, a method is provided. The method comprises receiving an electrocardiogram signal; analyzing a first frequency domain transform of the electrocardiogram signal sampled over a first time period to determine a first metric indicative of a metabolic state of a myocardium of the subject during the first time period; analyzing a second frequency domain transform of the electrocardiogram signal sampled over a second time period that is subsequent to the first time period to determine a second metric indicative of the metabolic state of the myocardium of the subject during the second time period; comparing the first metric to the second metric to determine whether the metabolic state of the myocardium of the subject is improving; and indicating, responsive to a determination that the metabolic state of the myocardium is not improving, administration of an intervention to the subject.

In accordance with another aspect of the present invention, a method of determining effectiveness of an intervention administered to a subject is provided. The method comprises receiving an electrocardiogram signal of the subject during administration of the intervention; analyzing a first frequency domain transform of the electrocardiogram signal sampled over a first time period to determine a first metric indicative of a metabolic state of a myocardium of the subject during the first time period; analyzing a second frequency domain transform of the electrocardiogram signal sampled over a second time period that is subsequent to the first time period to determine a second metric indicative of the metabolic state of the myocardium of the subject during the second time period; and comparing the first metric to the second metric to determine whether the metabolic state of the myocardium of the subject is one of improving, worsening, and remaining substantially the same.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having,"

"containing," "involving," and variations thereof herein is meant to encompass the items listed thereafter and equivalents thereof as well as additional items.

As described in the '856 patent, a spectral analysis of VF waveforms obtained from a subject's ECG may be used to predict when defibrillation is likely to be successful in restoring a perfusing cardiac rhythm of the subject, as well as to predict when defibrillation is likely to not be successful in restoring a perfusing cardiac rhythm. Although the '856 patent describes a variety of different metrics that may be used to predict the probability of success or failure of defibrillation to restore a perfusing cardiac rhythm, the area of the amplitude spectrum (ASA or AMSA) of the VF waveform has been shown to have a high positive predictive value (i.e., the ability to correctly predict that defibrillation is likely to restore a perfusing cardiac rhythm) as well as a high negative predictive value (i.e., the ability to correctly predict that defibrillation is unlikely to restore a perfusing cardiac rhythm). A further advantage of AMSA values as an indicator of the probability of success or failure of defibrillation is that AMSA values may be determined from an ECG that is obtained during the performance of chest compressions, and further, the subject's ECG may be filtered (e.g., using a band pass filter with a pass band between approximately 2 to 40 Hz) to remove artifacts relating to chest compressions without impacting the predictive capability of the AMSA values calculated therefrom.

Applicant has appreciated that a high AMSA value reflects a better metabolic state of the myocardial cells. Further, Applicant has identified that high quality chest compressions can increase AMSA values, as such high quality chest compressions create blood flow to the ischemic myocardium, thereby improving its metabolic state. Accordingly, AMSA values may be used as an indicator of the efficacy of chest compressions, or other forms of intervention, such as the introduction of a metabolite and/or a metabolic enhancing agent, the introduction of a thrombolytic agent, the electromagnetic stimulation of cardiac tissue at energy levels below those sufficient to defibrillate the heart, or combinations thereof.

Although high quality chest compressions can create blood flow to an ischemic myocardium, they may not be successful in certain situations. For example, some cardiac arrests may be caused by an acute blockage of a coronary artery (termed acute myocardial infarction). Where an acute blockage is present, even high quality chest compressions may not be successful in restoring blood flow to the region of the myocardium that is supplied by the blocked vessel because the blockage prevents it. Thus, where an acute blockage is suspected, or where other resuscitation efforts have proven unsuccessful, a thrombolytic agent, such as Tissue Plasminogen Activator (TPA) or recombinant TPA (rTPA) may be injected to break down or dissolve the blockage. Although the introduction of a thrombolytic agent may ultimately dissolve the blockage and permit the restoration of blood flow to the ischemic region of the myocardium, it cannot do so immediately, as the process of thrombolysis generally takes twenty minutes or more. During this time period of time, continued chest compressions are recommended.

Because AMSA values may be used to identify an improved metabolic state of myocardial cells due to chest compressions, Applicant has appreciated that AMSA values may also be used to identify an improved metabolic state of myocardial cells due to the re-opening of a blocked vessel. Accordingly, AMSA values as well as other metrics indicative of the metabolic state of a subject's myocardial cells may be used not only to predict the probability of success or failure of defibrillation to restore the subject's perfusing cardiac rhythm, but to identify when introduction of a thrombolytic agent should be attempted, as well as to identify when the thrombolytic agent is achieving success at breaking down the blockage. In addition, changes in a subject's AMSA values over time may be used to adjust the amount of thrombolytic agent introduced, the time at which it is introduced, or the manner of introduction (e.g., bolus or drip).

For example, if, during early application of CPR, it is determined that chest compressions do not lead to an increase in AMSA values, then this lack of an increase in AMSA values may be viewed as an indication of vascular blockage, and lysis (i.e., the injection of a thrombolytic agent) may be attempted earlier than it is typically done today (where lysis is generally used in a last-ditch effort to save the life of a subject), such as when other attempts at resuscitation have proven unsuccessful. After applying lysis, typical CPR cycles may be suspended and chest compressions performed until AMSA values increase. Such an increase in AMSA values may be viewed as an indication of the re-opening of a previously blocked coronary vessel. When the AMSA values rise to a level where the probability of successful defibrillation is indicated, defibrillation may then be attempted. It should be appreciated that by monitoring AMSA values or other indicators of the metabolic state of myocardial cells, defibrillation attempts that are likely to be unsuccessful may be avoided, thereby reducing the cellular damage that is associated with repeated defibrillation shocks. In addition, the avoidance of defibrillation shocks during periods in which they are unlikely to be successful reduces hands-off time (i.e., the period of time where chest compressions may be discontinued before and after defibrillation in an effort to obtain a clearer ECG without artifacts of chest compressions, and/or to avoid exposing a rescuer or other emergency personnel to defibrillating shocks), which further increases the subject's chances of survival.

It should be appreciated that AMSA values may be used to identify an improved metabolic state of myocardial cells due to other forms of intervention, other than the introduction of a thrombolytic agent or the application of CPR. Such other forms of intervention may include the introduction of a metabolite such as aspartate, glucose, nicotinamide adenine dinucleotide (NAD+), proglycogen, or 2-oxoglutarate, the introduction of a metabolic enhancing agent such as epinephrine, insulin, norepinephrine, etc., the application of electromagnetic energy to stimulate cardiac tissue at energy levels below those sufficient for defibrillation (termed "microperfusion" herein), or combinations thereof, such as described in commonly owned published U.S. application number US2005/0234515, which is incorporated herein by reference in its entirety.

Figure 1A:
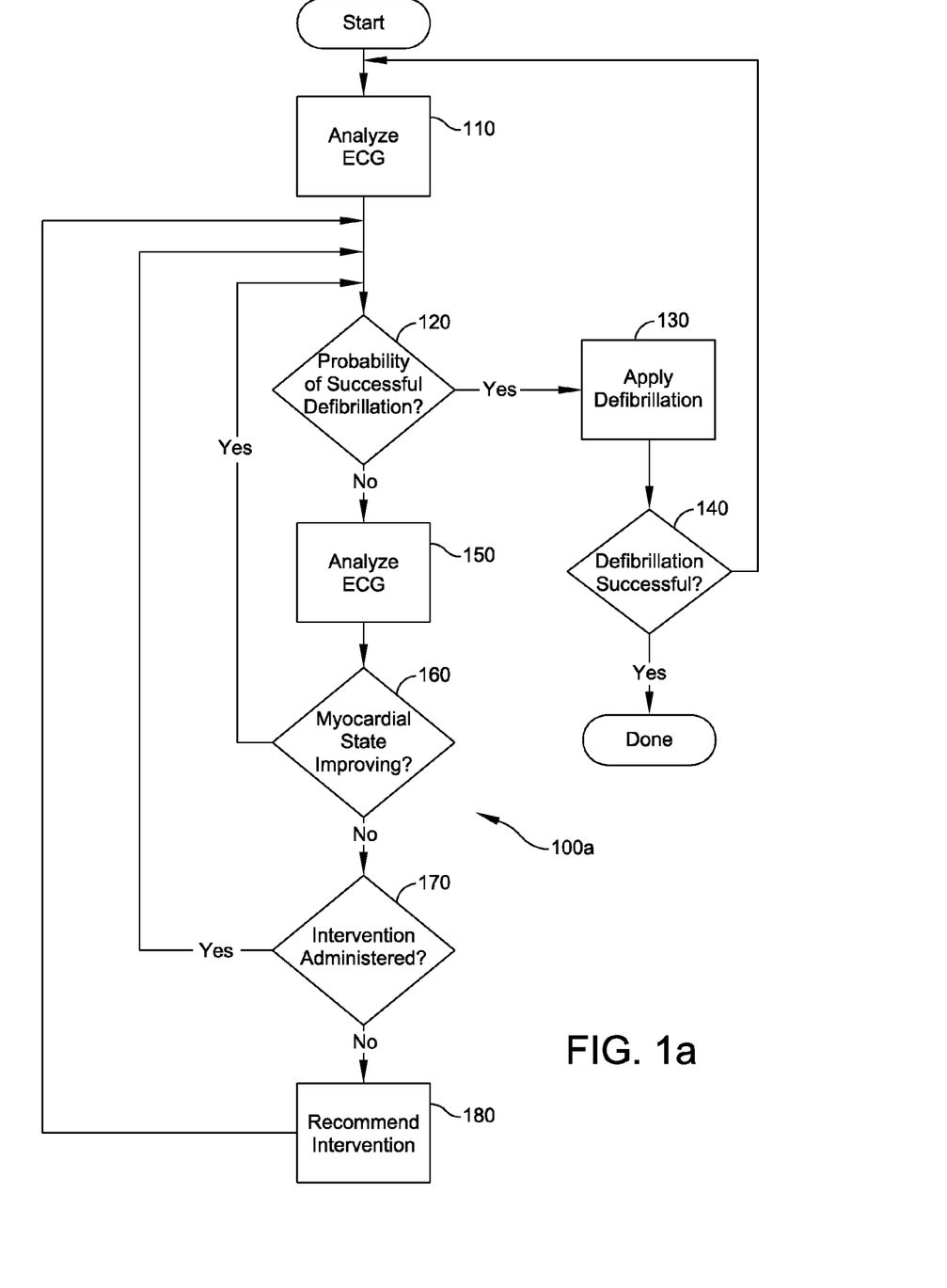
FIG. 1a is a flowchart showing a resuscitation routine that may be performed to guide resuscitation of a subject experiencing cardiac arrest according to an example embodiment of the invention.

FIG. 1a is a flowchart showing a resuscitation routine 100a that may be performed to guide resuscitation of a subject experiencing cardiac arrest according to an example embodiment of the invention. The resuscitation routine 100a may be performed by a life support device, such as an Advanced Life Support (ALS) defibrillator. During performance of the resuscitation routine 100a, chest compressions are continuously performed, except during those periods of time in which defibrillation is applied to the subject. The chest compressions may be performed manually by emergency responders, or with the aid of a chest compression device, such as the AutoPulse® Non-invasive Cardiac Support Pump available from Zoll Medical Corporation, of Chelmsford, Mass. Where the life support device is capable of performing defibrillation without interrupting the performance of chest compressions, the chest compressions may be performed continuously during performance of the resuscitation routine 100a.

In act 110, after ECG leads are attached to the body of the subject, the resuscitation routine analyzes the ECG of the subject. Analysis that may be performed in act 110 can include analyzing the ECG signals to identify whether a regular heart rhythm is detected (in which case, the routine may immediately terminate as defibrillation is not necessary), and whether a cardiac condition that is treatable by defibrillation (e.g., a 'shockable' ECG rhythm such as VT or VF) is present. Where a condition that is treatable by defibrillation is present, act 110 can include analyzing the subject's ECG signals over a period of time in the manner described in the '856 patent to determine AMSA values. In general, subjects with an AMSA value of about 21 mV*Hz have a statistically good chance of survival with typical interventions, those with an AMSA value of approximately 12 have about a 50% chance of survival, and those with AMSA values below about 7 are statistically unlikely to survive. It should be appreciated that in act 110, metrics other than AMSA values may be determined, such as Power Spectrum Area (PSA) or Average (or Median) peak-to-trough Amplitude (AM), instead or in addition to AMSA values.

In act 120, where a condition that is appropriately treated by defibrillation is present, the resuscitation routine determines a probability of successful defibrillation based upon the analysis of the subject's ECG performed in act 110. The determination made in act 120 may be based upon an evaluation of a single metric, such as the subject's AMSA values, or upon an evaluation of a number of different metrics. Where it is determined in act 120 that the probability of successful defibrillation meets or exceeds a certain threshold, for example 80%, the routine proceeds to act 130 wherein defibrillation is applied to the subject.

In act 140, a determination is made as to whether the defibrillation applied in act 130 was successful. Such a determination may be made based upon further analysis of the subject's ECG, by monitoring the subject's respiration, pulse, or other vital signs, or combinations thereof. Where it is determined in act 140 that defibrillation was successful, the routine may terminate, although it should be appreciated that the life support device may continue to monitor the vital signs of the subject.

Alternatively, where it is determined in act 120 that no condition treatable by defibrillation is present, or that the probability of successful defibrillation is at or below a certain threshold, for example, 20%, defibrillation is not performed, and the routine proceeds to act 150. As discussed further below, thresholds other than 80% and 20% may be used, such that defibrillation may be performed when the probability of success is above a determined threshold (e.g., 50%), and not performed when the probability of success is below the determined threshold.

In act 150, the resuscitation routine again analyzes the ECG of the subject. The analysis performed in act 150 can include identifying whether a regular heart rhythm is detected (in which case, the routine may immediately terminate as defibrillation is not necessary), and whether a cardiac condition that is treatable by defibrillation (e.g., VT or VF) is present. Where a condition that is treatable by defibrillation is present, act 150 can further include analyzing the subject's ECG signals over a period of time in the manner described in the '856 patent to determine AMSA values, or other metrics indicative of the metabolic state of the subject's myocardium. It should be appreciated that the analysis performed in act 150 may be similar to the analysis performed in act 110 described above, but it is performed over a period of time that is later than the analysis performed in act 110. Because the analysis performed in act 150 is performed over a different and subsequent period of time than that performed in act 110, the analysis performed in act 150 can be compared to the prior analysis performed in act 110 to detect any improvement, or worsening of the metabolic state of the subject's myocardium. It should be appreciated that the difference in time between acts 110 and 150 (or between successive iterations of act 150) can vary depending upon the type of intervention being used and the timeframe in which the intervention may be expected to take effect. In general, the difference in time between acts 110 and 150 (or between successive iterations of act 150) would typically be on the order of about 30 seconds to about three minutes, so as to detect changes in the metabolic state of the myocardium.

In act 160, a comparison between the metrics determined in acts 110 and 150 (or between successive iterations of act 150 is performed to determine whether the metabolic state of the subject's myocardium is improving, remaining substantially the same, or worsening. A number of different comparisons may be made in act 160, dependent, for example, on the particular type of intervention, the timeframe in which the particular type of intervention may be expected to take effect, etc. For example, where the type of intervention can be expected to take effect over a relatively short time frame (e.g., a few minutes), a comparison of the change in AMSA values over time (e.g., the change in AMSA values over successive iterations of act 150) may be used to detect whether the metabolic state of the subject's myocardium is improving or not. Such a comparison of the slope of the change in AMSA values over time may be appropriate for interventions such as the administration of metabolites or metabolic enhancements that generally take effect over shorter durations of time. For other types of interventions that generally take effect over longer durations of time, a different type of comparison may be used. For example, where the intervention is the administration of a thrombolytic agent that may take ten or twenty minutes to take effect, and for which the effects of successful thrombolysis may be reflected as a step increase in AMSA values, a different type of comparison, such as change point analysis may be used. As known to those skilled in the art, change point analysis is capable of detecting small changes in noisy data with minimal delay and good accuracy, such as would be likely during thrombolysis.

Where it is determined in act 160 that the metabolic state of the subject's myocardium is improving, the routine returns to act 120, wherein acts 120, 150, and 160 may again be performed until the probability of successful defibrillation meets or exceeds the threshold (act 120) and acts 130 and 140 are performed. Alternatively, where it is determined in act 160 that the metabolic state of the subject's myocardium is not improving (that is, where it is determined that the metabolic state of the subject's myocardium remains essentially the same, or is worsening), the routine proceeds to act 170.

In act 170 a determination is made as to whether an intervention, such as the introduction of a thrombolytic agent such as TPA or rTPA, a metabolite, or a metabolic enhancing agent to the body of the subject has previously been administered, such as by injection or infusion. Such a determination may be made by the ALS device visually or audibly prompting an emergency responder to indicate whether a thrombolytic agent or other type of intervention has been administered and awaiting a response. Where it is determined that a thrombolytic agent or other type of intervention has previously been administered, the routine returns to act 120. The acts described above may be repeated and the subject's ECG repeatedly analyzed in successive iterations of act 150 to determine whether the administered thrombolytic agent or other type of intervention is achieving any success in improving the metabolic state of the subject's myocardium and to allow the thrombolytic agent or other type of intervention time to take effect.

Alternatively, where it is determined in act 170 that a thrombolytic agent or other type of intervention has yet to be administered to the subject, the routine proceeds to act 180, wherein the routine prompts the emergency responder or other care giver to administer an intervention to the body of the subject. For example, in act 180, the ALS device may visually or audibly prompt the emergency responder to administer a thrombolytic agent, and may even recommend a particular type of thrombolytic agent and dosage amount, based upon recommended guidelines and/or the prior analysis of the subject's myocardial condition. After prompting the emergency responder to administer the thrombolytic agent or other type of intervention, the routine proceeds to act 120 wherein the acts described above may be repeated. The acts described above may be repeated and the subject's ECG repeatedly analyzed in successive iterations of act 150 to determine whether the administered thrombolytic agent or other type of intervention is achieving any success in improving the metabolic state of the subject's myocardium and to allow the thrombolytic agent or other type of intervention time to take effect.

It should be appreciated that the resuscitation routine 100a described above is not limited to the acts described above with respect to FIG. 1a, as one or more of the acts may be modified, and other acts may be added without departing from the scope of the method described herein. For example, after an analysis of the subject's ECG is performed in act 110 and a shockable rhythm is detected, the subject may be shocked immediately in an attempt to restore a regular heartbeat without any determination of the probability of success. If this initial attempt at defibrillation is unsuccessful, the routine may then proceed as described above. Moreover, it should be appreciated that the thresholds of 80% and 20% used in act 120 are purposefully conservative, and are set to a level to maximize the probability of successful defibrillation while minimizing damage to the subject's myocardium, and other values could be used. For example, as long as the probability of success was equal or greater than a certain threshold (e.g., 50%), defibrillation may be applied, and defibrillation not applied if the probability of success was less than this threshold. Alternatively, where the probability of success is less than a first threshold (e.g., 80%) but greater than a second threshold (e.g., 20%), the routine could audibly or visually alert the rescuer to the determined probability and request their input on whether to apply defibrillation or not. Where the resuscitation routine is performed by a device that does not have the ability to apply defibrillation, such as where the resuscitation routine is performed by a cardiac monitor, act 130 could be modified to audibly or visually prompt the user (e.g., an emergency responder) to apply defibrillation using a standalone defibrillator.

Figure 1B:
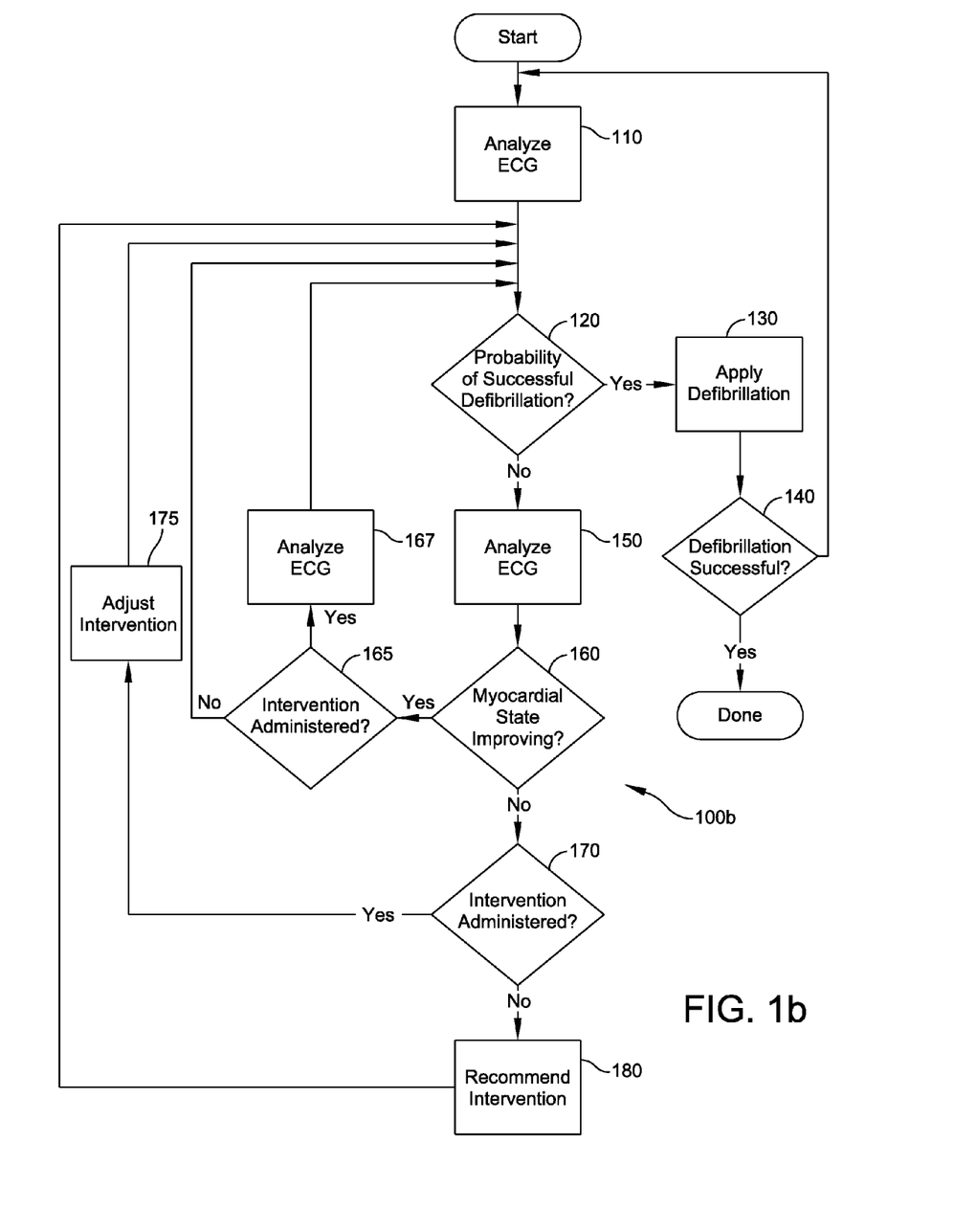
FIG. 1b is a flowchart of an alternative resuscitation routine that may be performed to guide resuscitation of a subject experiencing cardiac arrest according to an example embodiment of the invention.

Other modifications to the resuscitation routine 100a of FIG. 1a may include acts of adjusting a level of the intervention that is applied to the subject in response to the myocardial state of the subject improving, or in response to the myocardial state remaining the same, or declining. For example, FIG. 1b is a flowchart showing an alternative resuscitation routine 100b that may be performed to guide the resuscitation of a subject experiencing cardiac arrest in which the level of intervention administered to the subject may be adjusted based upon the myocardial state of the subject. As in the resuscitation routine 100a described previously with respect to FIG. 1a, the resuscitation routine 100b may be performed by a life support device, such as an Advanced Life Support (ALS) defibrillator. During performance of the resuscitation routine 100b, chest compressions are performed continuously, where such is possible. As the resuscitation routine 100b of FIG. 1b is substantially similar to the resuscitation routine 100a of FIG. 1a, only the differences are discussed in detail herein.

In act 110, after ECG leads are attached to the body of the subject, the resuscitation routine analyzes the ECG of the subject. Analysis that may be performed in act 110 can again include analyzing the ECG signals to identify whether a regular heart rhythm is detected (in which case, the routine may immediately terminate as defibrillation is not necessary), and whether a cardiac condition that is treatable by defibrillation (e.g., a 'shockable' ECG rhythm such as VT or VF) is present. Where a condition that is treatable by defibrillation is present, act 110 can include analyzing the subject's ECG signals to determine AMSA values or other metrics, such as Power Spectrum Area (PSA) and Average (or Median) peak-to-trough Amplitude (AM).

In act 120, where a condition that is appropriately treated by defibrillation is present, the resuscitation routine determines a probability of successful defibrillation based upon the analysis of the subject's ECG performed in act 110. The determination made in act 120 may be based upon an evaluation of a single metric, such as the subject's AMSA values, or upon an evaluation of a number of different metrics. Where it is determined in act 120 that the probability of successful defibrillation meets or exceeds a certain threshold, the routine proceeds to acts 130 and 140 as described previously with respect to FIG. 1a.

Alternatively, where it is determined in act 120 that no condition treatable by defibrillation is present, or that the probability of successful defibrillation is at or below a certain threshold, defibrillation is not performed, and the routine proceeds to act 150, wherein the resuscitation routine again analyzes the ECG of the subject in the manner discussed previously. As previously described with respect to FIG. 1a, the analysis performed in act 150 may be similar to the analysis performed in act 110, but it is performed over a period of time that is later than the analysis performed in act 110.

In act 160, a comparison between the metrics determined in acts 110 and 150 (or between successive iterations of act 150) is performed to determine whether the metabolic state of the subject's myocardium is improving, remaining substantially the same, or worsening. As noted previously with respect to FIG. 1a, this determination may be based upon a change in slope of AMSA values over time, or a change point analysis of AMSA values, dependent on the type of intervention applied. Where it is determined in act 160 that the metabolic state of the subject's myocardium is improving, the routine proceeds to act 165 wherein a further determination is made as to whether an intervention has previously been administered (e.g., responsive to act 180 as described below) to the subject. Where it is determined in act 165 that an intervention has not been administered, the routine returns to act 120, wherein acts 120, 150, 160, and 165 may again be performed until the probability of successful defibrillation meets or exceeds the threshold (act 120) and acts 130 and 140 are performed.

Alternatively, where it is determined in act 165 that an intervention has been administered and is having a beneficial effect (i.e., act 160 Yes), the amount of the intervention that is being applied to the subject may be adjusted in act 167. The adjustment that is made in act 167 may be upward or downward, dependent on the type of intervention, as well as other factors. For example, where the intervention that is recommended in act 180 is the administration of a thrombolytic agent, such as TPA or rTPA, the recommendation may be to apply a bolus dose of the thrombolytic agent to the body of the subject, followed by an IV infusion at a particular rate, up to a determined maximum dosage. Where it is determined that the administration of the thrombolytic agent is having a beneficial effect (act 160 Yes), the infusion rate of the thrombolytic agent may be reduced or terminated in an effort to reduce the amount of trauma to the subject that results from the thrombolytic properties of the agent in combination with the physical trauma caused by other resuscitation efforts, such as CPR and defibrillation. Alternatively, where the intervention that is recommended in act 180 is the administration of metabolite or a metabolic enhancing agent (for example in a bolus dose followed by an IV drip or infusion at a particular rate up to a determined maximum dosage), the adjustment performed in act 167 may be upward so as to accelerate the improvement, given that such metabolites or metabolic enhancing agents may have fewer and shorter duration side effects. In this manner, AMSA values indicative of the metabolic state of a subject's myocardium may be used to identify whether a particular type of intervention is being successful, and to guide the amounts and timing used to administer the particular type of intervention. After adjusting the intervention in act 167, the routine returns to act 120, wherein acts 120, 150, 160, 165, and 167 may again be performed until the probability of successful defibrillation meets or exceeds the threshold (act 120) and acts 130 and 140 are performed.

As with the resuscitation routine 100a of FIG. 1a, where it is determined in act 160 that the metabolic state of the subject's myocardium is not improving (that is, where it is determined that the metabolic state of the subject's myocardium remains essentially the same, or is worsening), the routine proceeds to act 170. In act 170 a determination is made as to whether an intervention, such as the administration of a thrombolytic, metabolic, or metabolic enhancing agent to the body of the subject has previously been administered, such as by injection or infusion. As described previously, such a determination may be made by the ALS device visually or audibly prompting an emergency responder or other care giver to indicate whether a thrombolytic agent or other type of intervention has been administered and awaiting a response. Where it is determined that a thrombolytic agent or other type of intervention has previously been administered, the routine proceeds to act 175.

Where it is previously determined in act 170 that an intervention has been administered (i.e., act 170 Yes) and that intervention does not appear to be having any beneficial effect (i.e., act 160 No), the amount of the intervention that is being applied to the subject may be adjusted in act 175. The adjustment that is made in act 175 may be upward or downward (or not at all), dependent on the type of intervention, the amount of time for which the intervention has been performed, etc. For example, where the intervention that is recommended in act 180 is the administration of a thrombolytic agent, such as TPA or rTPA, the recommendation may be to apply a bolus dose of the thrombolytic agent to the body of the subject, followed by an IV infusion at a particular rate, up to a determined maximum dosage. Where it is determined that the administration of the thrombolytic agent has yet to have a beneficial effect (act 160 No), the infusion rate of the thrombolytic agent may be increased, or an additional bolus dose may be provided, up to the maximum dosage. Alternatively, where the maximum dosage has been reached, or where the amount of time for which the intervention has been performed is sufficient to have had a beneficial effect, the intervention may be adjusted downward, or not at all. After adjusting the intervention in act 175, the routine returns to act 120, wherein acts 120, 150, 160, and any of act 165, 167, 170, and 175 may again be performed until the probability of successful defibrillation meets or exceeds the threshold (act 120) and acts 130 and 140 are performed. The acts described above may be repeated and the subject's ECG repeatedly analyzed in successive iterations of act 150 to determine whether the administered thrombolytic agent or other type of intervention is achieving any success in improving the metabolic state of the subject's myocardium and to allow the thrombolytic agent or other type of intervention time to take effect.

Alternatively, where it is determined in act 170 that a thrombolytic agent or other type of intervention has yet to be administered to the subject, the routine proceeds to act 180, wherein the routine prompts the emergency responder or other medical personnel to administer an intervention to the body of the subject. For example, as previously described, in act 180, the ALS device may visually or audibly prompt the emergency responder to administer a thrombolytic agent, and may even recommend a particular type of thrombolytic agent and dosage amount, based upon recommended guidelines and/or the prior analysis of the subject' myocardial condition. After prompting the emergency responder to administer the thrombolytic agent or other type of intervention, the routine proceeds to act 120 where the acts described above may be repeated.

As described with respect to FIG. 1b above, changes in AMSA values over time may be used to detect the success (or lack of success) of a particular type of intervention. Such changes may then be used to adjust the level, the timing, or both the level and timing at which the particular type of intervention is being administered (e.g., to adjust a dosage of thrombolytic agent being provided to the subject) based on the detected success (or lack thereof).

As with the resuscitation routine of FIG. 1a, it should be appreciated that the resuscitation routine 100b described above is not limited to the acts described above as one or more of the acts may be modified, and other acts may be added without departing from the scope of the method described herein. For example, where a particular type of intervention is administered and found not to improve the metabolic state of the subject's myocardium within a timeframe in which it could have, an alternative type of intervention may be recommended. Moreover, other modifications, such as those previously discussed with respect to the resuscitation routine 100a may also be readily envisioned.

Although the monitoring of AMSA values or other metrics indicative of the metabolic state of a subject's myocardium over time may be used to guide resuscitation efforts in the manner discussed above with respect to FIGS. 1a and 1b, they may more generally be used as an indicator for guiding therapy. For example, AMSA values may be used to monitor a subject's myocardial state and to maintain that state within a desired range. For example, one might want to maintain a subject's AMSA values at a specific number, or within a specific range of values by delivering metabolic agents. The metabolic state of the subject's heart will generally increase following the delivery of the metabolic agents, but will then fall back after a few minutes. However, by monitoring the subject's AMSA values, the amount and/or timing of the delivery of the metabolic agents may be adjusted so as to maintain the metabolic state of the subject's heart in a desired state corresponding to a particular range of AMSA values.

Figure 2:
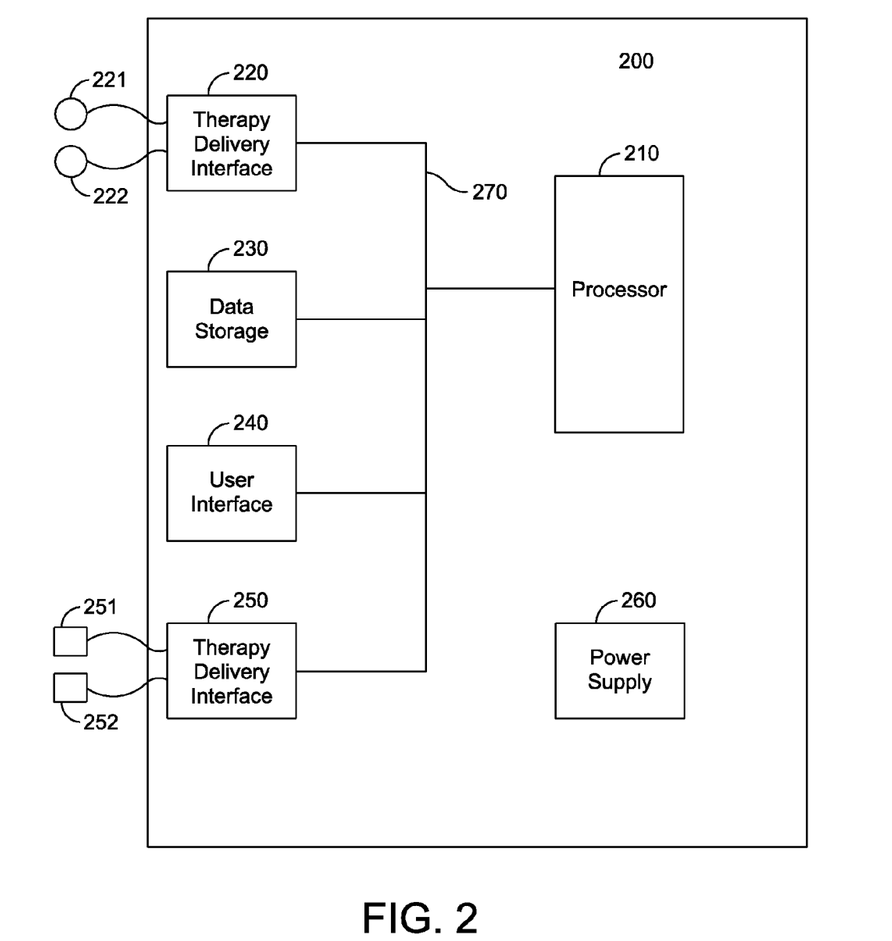
FIG. 2 is a functional block diagram of an advanced lifesaving device that may be used to implement the resuscitation routines of FIGS. 1a and 1b according to an example embodiment of the invention.

FIG. 2 is a block diagram of an ECG monitoring system that can be used to monitor and analyze a subject's ECG signal in accordance with the resuscitation routines of FIGS. 1a and 1b. The ECG monitoring system may be configured for use as a standalone monitor, or integrated into an ALS device 200 as shown in FIG. 2.

As shown in FIG. 2, the ALS device 200 includes a processor 210, a sensor interface 220, data storage 230, a user interface 240, a therapy delivery interface 250, and a power supply 260. The processor 210, the sensor interface 220, the storage device 230, the user interface 240, and the therapy delivery interface 250 are coupled together via a bus 270. The power supply 260 may be a conventional AC to DC power supply capable of providing power to the other device components, or where the ALS device 200 is a portable ALS device, the power supply 260 may include a DC power supply, such as a battery. The data storage 230 includes a computer readable and writeable data storage medium configured to store non-transitory instructions and other data (such as AMSA values determined in acts 110 and 150 of FIGS. 1a and 1b), and can include both nonvolatile storage media, such as optical or magnetic disk, ROM or flash memory, as well as volatile memory, such as RAM. The instructions may include executable programs or other code that can be executed by the processor 210 to perform any of the functions described above with respect to the resuscitation routine of FIGS. 1a and 1b.

The processor 210 may be any type of processor, microprocessor, or controller, such as a microprocessor commercially available from such companies such as Texas Instruments, Intel, AMD, Sun, IBM, Motorola, Freescale, ARM Holdings, etc. In one implementation, the processor is a DSP processor, such as a Freescale DSP56311 Digital Signal Processor, that is capable of performing the acquisition and spectral analysis of ECG signals. The processor 210 is configured to monitor the subject's medical condition, to perform medical data logging, analysis and storage, and to provide medical treatment to the subject in response to a detected medical condition, such as cardiac arrhythmia.

The sensor interface 220 couples the at least one processor 210 to a plurality of physiological sensors, such as a plurality of ECG sensing electrodes 221, 222 that are attached to the body of the subject. In some embodiments, the sensor interface 220 may also couple the processor 210 to other physiological sensors, such as activity sensors, pulse oxygen sensors, temperature sensors, respiratory rate sensors, thoracic impedance sensors, blood pressure sensors, acoustic sensors, etc. The sensor interface 220 will typically include one or more amplifiers to buffer, amplify, and/or filter the ECG signals of the subject. The sensor interface 210 also includes an Analog to Digital (A/D) converter to sample and digitize the subject's ECG signal and provide the digitized samples of the subject's ECG signal to the processor 210. Although the sensor interface 220 has been described as including various electronic circuitry capable of buffering, amplifying, filtering, and digitizing the ECG signals of the subject, those of ordinary skill in the art should appreciate that one or more of those functions could alternatively be performed elsewhere in the ALS device 200.

The therapy delivery interface 250 couples one or more therapy delivery devices, such as defibrillator electrodes 251, 252, that may be attached to the subject's chest, to the processor 210. In an embodiment, the therapy delivery interface 250 is capable of delivery a biphasic defibrillating shock to the body of the subject.

The user interface 240 includes a combination of hardware and software components that allow the ALS device 200 to communicate with a user, such as an emergency responder. These components are configured to provide guidance or instruction (visually or audibly) to the user, and to receive information and/or feedback (visually, audibly, or haptically) from the user. Examples of the components that may be employed within the user interface 240 include keyboards, mouse devices, trackballs, microphones, touch-sensitive display screens, conventional display screens, and speakers.

In use, the plurality of ECG sensing electrodes 221, 222 and the defibrillation electrodes 251, 252 are placed on the body of the subject. Signal processing circuitry within the sensor interface 220 buffers, amplifies, and in some embodiments, filters the subject's ECG signal, and samples of the processed ECG signal are digitized by an A/D converter and provided to the processor 210. The processor 210 analyzes the digitized ECG signal to determine whether a normal cardiac rhythm is present, and if not, to determine whether a cardiac condition that is treatable by defibrillation (such as VT or VF) is present. The processor 210 may display the digitized ECG signal on a display associated with the user interface 240. Where the processor 210 determines that treatable cardiac condition is present, the processor 210 transforms the time domain samples of the subject's ECG signal to the frequency domain, for example, by using a fast Fourier transform (FFT), and calculates one or more metrics that based upon an spectral analysis of the transformed ECG signal. The metrics that are calculated by the processor 210 may include AMSA values, PSA values, or other metrics indicative of the probability of successful defibrillation and the metabolic state of the subject's myocardium. Where the processor determines that the probability of successful defibrillation is sufficiently high as to warrant the application of a defibrillating shock, the processor 210 may instruct the therapy delivery interface 250 to do so. Alternatively, where the probability of successful defibrillation is low, the processor may send a message to be presented by the user interface 240 recommending the administration of a thrombolytic agent or other type of intervention to the subject if one has not been previously administered.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A system comprising:
   a sensor interface configured to receive and process an analog electrocardiogram signal of a subject and provide a digitized electrocardiogram signal; and
   a processor, coupled to the sensor interface, the processor being configured to perform operations comprising:
   receiving the digitized electrocardiogram signal, analyzing a frequency domain transform of the digitized electrocardiogram signal sampled over a first time period to determine whether ventricular fibrillation waveforms are present within the electrocardiogram signal sampled over the first time period, in response to determining that the ventricular fibrillation waveforms are present, determining a first metric indicative of a first metabolic state of a myocardium of the subject based on the ventricular fibrillation waveforms, indicating administration of an intervention to the subject in response to a determination that the first metric is outside a predetermined range, periodically analyzing additional frequency domain transforms of the digitized electrocardiogram signal sampled over additional subsequent time periods that are after the first time period to determine whether subsequent ventricular fibrillation waveforms are present within the electrocardiogram signal sampled over the subsequent time periods, in response to determining that the subsequent ventricular fibrillation waveforms are present, determining a subsequent metric indicative of a subsequent metabolic state of the myocardium of the subject based on the subsequent ventricular fibrillation waveforms, comparing the first and subsequent metrics to determine whether the subsequent metabolic state changed relative to the first metabolic state of the myocardium of the subject, and indicating a modification in the administration of the intervention to the subject to maintain the subsequent metric in the predetermined range.

2. The system of claim 1, wherein the processor is further configured to periodically analyze the additional frequency domain transforms of the digitized electrocardiogram signals at a frequency based on a type of the intervention.

3. The system of claim 1, wherein the administration of the intervention is an administration of a metabolic agent.

4. The sensor interface of claim 3, wherein the modification in the administration of the intervention includes a change in an amount of the metabolic agent delivered to the subject.

5. The system of claim 3, wherein the modification in the administration of the intervention includes a change in timing of delivery of the metabolic agent to the subject.

6. The system of claim 3, wherein the modification in the administration of the intervention includes a modification to a manner of delivery of the metabolic agent to the subject.

7. The system of claim 3, wherein the administration of the metabolic agent is an administration of a thrombolytic agent.

8. The system of claim 1, wherein the processor is further configured to modify the administration of the intervention to the subject as needed to bring the subsequent metric into the predetermined range.

9. The system of claim 1, wherein the first metric comprises an amplitude spectral area of the ventricular fibrillation waveforms of the digitized electrocardiogram signal sampled over the first time period.

10. The system of claim 1, wherein the subsequent metric comprises a subsequent amplitude spectral area of the ventricular fibrillation waveforms of the electrocardiogram signal sampled over the subsequent time periods.

11. A method of treating a subject, the method comprising:

receiving a digitized electrocardiogram signal from the subject;

analyzing a frequency domain transform of the digitized electrocardiogram signal sampled over a first time period to determine whether ventricular fibrillation waveforms are present within the electrocardiogram signal sampled over the first time period;

in response to determining that the ventricular fibrillation waveforms are present, determining a first metric indicative of a first metabolic state of a myocardium of the subject based on the ventricular fibrillation waveforms;

indicating administration of an intervention to the subject in response to a determination that the first metric is outside a predetermined range, periodically analyzing additional frequency domain transforms of the digitized electrocardiogram signal sampled over additional subsequent time periods that are after the first time period to determine whether subsequent ventricular fibrillation waveforms are present within the electrocardiogram signal sampled over the subsequent time periods;

in response to determining that the subsequent ventricular fibrillation waveforms are present, determining a subsequent metric indicative of a subsequent metabolic state of the myocardium of the subject based on the subsequent ventricular fibrillation waveforms;

comparing the first and subsequent metrics to determine whether the subsequent metabolic state changed relative to the first metabolic state of the myocardium of the subject; and indicating a modification to the administration of the intervention to the subject to maintain the subsequent metric in the predetermined range.

12. The method of claim 11, wherein the additional frequency domain transforms of the digitized electrocardiogram signals are periodically analyzed at a frequency based on the type of intervention.

13. The method of claim 11, wherein indicating the administration of the intervention includes indicating administration of a metabolic agent.

14. The method of claim 13, wherein indicating the modification to the administration of the intervention includes indicating a change in an amount of the metabolic agent delivered to the subject.

15. The method of claim 13, wherein indicating the modification to the administration of the intervention includes indicating a change in timing of delivery of the metabolic agent to the subject.

16. The method of claim 13, wherein indicating the modification to the administration of the intervention includes indicating a modification to a manner of delivery of the metabolic agent to the subject.

17. The method of claim 11, further comprising modifying the administration of the intervention to the subject as needed to maintain the subsequent metric in the predetermined range.

* * * * *

UNITED STATES PATENT AND TRADEMARK OFFICE
CERTIFICATE OF CORRECTION

PATENT NO. : 9,743,855 B2
APPLICATION NO. : 14/594529
DATED : August 29, 2017
INVENTOR(S) : Gary A. Freeman and Ulrich Herken It is certified that error appears in the above-identified patent and that said Letters Patent is hereby corrected as shown below:

In the Claims

In Claim 4, Column 13, Line 40, please delete "sensor interface" and insert --system--.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*